US012594034B2

(12) United States Patent
Lee et al.

(10) Patent No.: US 12,594,034 B2
(45) Date of Patent: Apr. 7, 2026

(54) WEARABLE DEVICE AND METHOD FOR MEASURING BIOMETRIC INFORMATION

(71) Applicant: SAMSUNG ELECTRONICS CO., LTD., Suwon-si (KR)

(72) Inventors: Suho Lee, Suwon-si (KR); Jeongmin Park, Suwon-si (KR); Injo Jeong, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 389 days.

(21) Appl. No.: 18/109,020

(22) Filed: Feb. 13, 2023

(65) Prior Publication Data

US 2023/0190193 A1      Jun. 22, 2023

Related U.S. Application Data

(63) Continuation of application No. PCT/KR2021/011683, filed on Aug. 31, 2021.

(30) Foreign Application Priority Data

Aug. 31, 2020    (KR) ........................ 10-2020-0110276

(51) Int. Cl.
*A61B 5/00*          (2006.01)
*A61B 5/0533*        (2021.01)
(Continued)

(52) U.S. Cl.
CPC ............ *A61B 5/681* (2013.01); *A61B 5/0533* (2013.01); *A61B 5/282* (2021.01); *A61B 5/332* (2021.01); *A61B 5/7282* (2013.01); *A61B 5/742* (2013.01)

(58) Field of Classification Search
CPC ....... A61B 5/681; A61B 5/0533; A61B 5/282; A61B 5/7282; A61B 5/742
See application file for complete search history.

(56) References Cited

U.S. PATENT DOCUMENTS

| | | | |
|---|---|---|---|
| 9,423,418 B2 | 8/2016 | Alameh et al. | |
| 9,478,998 B1 * | 10/2016 | Lapetina ................ | H01R 24/62 |

(Continued)

FOREIGN PATENT DOCUMENTS

| | | |
|---|---|---|
| JP | 2017-006230 | 1/2017 |
| KR | 20-2016-0002493 | 7/2016 |

(Continued)

OTHER PUBLICATIONS

English Translation of WO 2016/136135A1.*

(Continued)

*Primary Examiner* — Catherine M Voorhees
(74) *Attorney, Agent, or Firm* — Nixon & Vanderhye P.C.

(57) ABSTRACT

According to the present disclosure, a wearable device is disclosed, the wearable device may include: a front surface including a display; a frame having the display seated therein and forming the sides of the wearable device, wherein the frame includes a plurality of conductive regions and a non-conductive region exposed between the plurality of conductive regions; a plurality of biosensors arranged in a space formed by the frame and electrically connected to the plurality of conductive regions; and a processor electrically connected to the plurality of biosensors, wherein the processor is configured to: identify occurrence of an event related to the acquisition of biometric information, identify, in response to the occurrence of the event, at least one conductive region for acquiring the biometric information (Continued)

110

301a
301b

301c among the plurality of conductive regions, and acquire the biometric information using the identified at least one conductive region.

13 Claims, 20 Drawing Sheets

(51) Int. Cl.
    *A61B 5/282*     (2021.01)
    *A61B 5/332*     (2021.01)

(56)           References Cited

U.S. PATENT DOCUMENTS

| | | |
|---|---|---|
| 10,474,195 B2 | 11/2019 | Lasyath et al. |
| 10,581,145 B2 | 3/2020 | Han et al. |
| 11,895,781 B1 * | 2/2024 | Davis .................. A61B 5/0535 |
| 2016/0235341 A1 | 8/2016 | Choi et al. |
| 2018/0217682 A1 | 8/2018 | Dangy Cave |
| 2018/0220923 A1 | 8/2018 | Shim et al. |
| 2018/0220967 A1 | 8/2018 | Wang et al. |
| 2019/0146415 A1 | 5/2019 | Ely et al. |
| 2019/0339860 A1 * | 11/2019 | Chen ................... G04G 9/0064 |
| 2021/0000376 A1 | 1/2021 | Lee et al. |
| 2021/0159651 A1 | 5/2021 | Ryu et al. |
| 2021/0177290 A1 | 6/2021 | Jung et al. |

FOREIGN PATENT DOCUMENTS

| | | | |
|---|---|---|---|
| KR | 10-2017-0010704 | 2/2017 | |
| KR | 10-2018-0018739 | 2/2018 | |
| KR | 10-2019-0097474 | 8/2019 | |
| KR | 10-2096804 | 3/2020 | |
| KR | 10-2021-0016875 | 2/2021 | |
| KR | 10-2021-0063120 | 6/2021 | |
| KR | 10-2021-0073929 | 6/2021 | |
| KR | 10-2022-0028907 | 3/2022 | |
| KR | 10-2440484 | 9/2022 | |
| WO | WO-2016136135 A1 * | 9/2016 | ............... A61B 5/02 |

OTHER PUBLICATIONS

International Search Report mailed Dec. 21, 2021 in PCT application PCT/KR2021/011683, 6 pages.
Written Opinion of the ISA mailed Dec. 21, 2021 in PCT application PCT/KR2021/011683, 4 pages.
Korean Office Action dated Sep. 3, 2025 for KR Application No. 10-2020-0110276.
Samsung Gear S3 User Manual dated Jul. 17, 2018; 100 pages.

* cited by examiner 148
146
142
140
193

110

401a

401b

401a

401b

START

_⌐610
IDENTIFY OCCURRENCE OF EVENT RELATED TO
ACQUISITION OF BIOMETRIC INFORMATION

_⌐620
IDENTIFY AT LEAST ONE CONDUCTIVE AREA
IN RESPONSE TO EVENT OCCURRENCE

_⌐630
ACQUIRE BIOMETRIC INFORMATION BY USING
IDENTIFIED CONDUCTIVE AREA

END

WEARABLE DEVICE AND METHOD FOR MEASURING BIOMETRIC INFORMATION

CROSS-REFERENCE TO RELATED APPLICATIONS

This application is a continuation of International Application No. PCT/KR2021/011683 designating the United States, filed on Aug. 31, 2021, in the Korean Intellectual Property Receiving Office and claiming priority to Korean Patent Application No. 10-2020-0110276, filed on Aug. 31, 2020, in the Korean Intellectual Property Office, the disclosures of which are incorporated by reference herein in their entireties.

BACKGROUND

Field

The disclosure relates to a technology for measuring biometric information using an electrode in a wearable electronic device.

Description of Related Art

In accordance with increasing interests in health, a biometric signal measurement function is becoming increasingly prevalent in electronic devices. Electronic devices may be attached to a user body to measure biometric information of the user. For example, the electronic devices may measure biometric information, such as a heart rate, a galvanic skin response (GSR), an electrocardiography (ECG), and a bioelectrical impedance of a user.

The electronic devices may use a biometric sensor for measuring biometric information. For example, the electronic devices may measure biometric information, such as an electrocardiography, a bioelectrical impedance, and a galvanic skin response using a biometric sensor, such as an ECG sensor, a BIA sensor, and a GSR sensor.

A frame of a wearable device may be formed of a metal material such as SUS or aluminum to enhance durability and have a design as a conventional analog watch in general. In order to configure multiple electrodes for measuring various biometric signals in addition to an ECG, the frame and the electrode of the wearable device need to be separated to prevent interference therebetween. To this end, it is necessary to divide the frame of the wearable device or configure a separate contact point such as a key. However, the more the frame of the wearable device is divided, the more the durability and waterproofness thereof may be degraded, and mounting a key on a lateral part of the frame may cause limitation in terms of space and design.

SUMMARY

A wearable device according to an example embodiment may include: a front surface including a display, a frame having the display seated therein and forming the sides of the wearable device, the frame including multiple conductive regions and a non-conductive regions exposed between the multiple conductive regions, multiple biometric sensors arranged in a space formed by the frame and electrically connected to the multiple conductive regions, and a processor electrically connected to the multiple biometric sensors, wherein the processor is configured to: identify occurrence of an event related to acquisition of biometric information, identify, in response to the occurrence of the event, at least one conductive region configured to acquire the biometric information among the multiple conductive regions, and control the wearable device to acquire the biometric information using the identified at least one conductive area.

A wearable device according to an example embodiment may include: a front surface including a display, a frame having the display seated therein and forming a lateral surface of the wearable device, the frame including multiple conductive areas and a non-conductive areas exposed between the multiple conductive areas, at least one grip sensor arranged in a space formed by the frame and electrically connected to the multiple conductive areas, and a processor electrically connected to the at least one grip sensor, wherein the processor is configured to: identify occurrence of an event for executing a designated operation, identify, in response to the occurrence of the event, a conductive area in contact with a first portion of a user body among the multiple conductive areas, and execute a designated operation in response to the identification of the contacted conductive area.

A wearable device in various example embodiments of the disclosure may be freely realized in terms of design by arranging multiple electrodes on a frame and provide various functions.

BRIEF DESCRIPTION OF THE DRAWINGS

The above and other aspects, features and advantages of certain embodiments of the present disclosure will be more apparent from the following detailed description, taken in conjunction with the accompanying drawings, in which.

DETAILED DESCRIPTION

Figure 1:
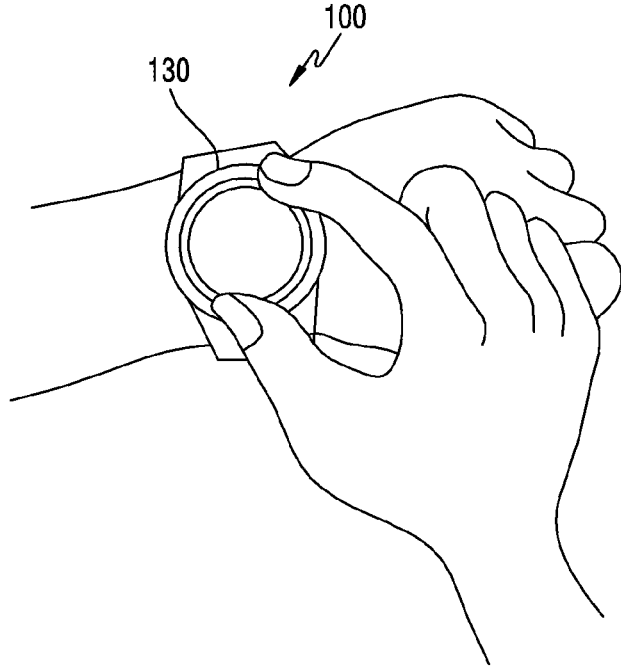
FIG. 1 is a diagram illustrating mounting of a wearable device on a portion of a human body according to various embodiments.

FIG. 1 is a diagram illustrating mounting of an example wearable device on a portion of a human body according to various embodiments.

According to an embodiment, the wearable device 100 in FIG. 1 may be a smart watch as shown in the drawing. However, without limitation thereto, the wearable device 100 may include various types of devices attachable to a body of a user to be used.

According to an embodiment, the wearable device 100 may include a strap 130 to be attached to the body of the user by allowing the strap 130 to be wound around a wrist of the user. However, without limitation thereto, the wearable device 100 may be attached to various body parts of the user according to a shape, a size, or the like of the wearable device 100. For example, the wearable device 100 may be attached to a hand, back of the hand, a finger, a fingernail, a fingertip, and the like, as well.

Figure 2A:
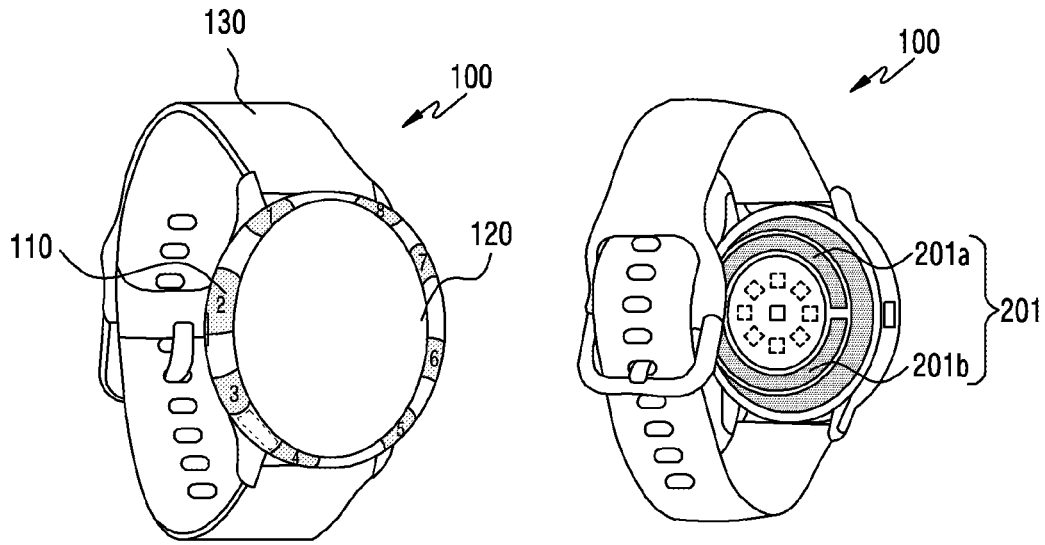
FIG. 2A is a perspective view illustrating a wearable device according to various embodiments.

FIG. 2A is a perspective view illustrating a wearable device according to various embodiments.

Referring to FIG. 2A, the wearable device 100 may include a frame 110, a display 120, and a strap 130. According to an embodiment, the wearable device 100 may omit at least one of components shown in the drawing or additionally include other components.

According to an embodiment, the frame 110 may include an upper surface, a lower surface, and a lateral surface surrounding a space between the upper surface and the lower surface. According to an embodiment, the frame 110 may be configured by various combinations. For example, the frame 110 may be configured by a combination of a lateral bezel structure 111, a wheel key 121, a rear plate 193, and a rear cover window 148 as illustrated, for example in FIG. 2B. According to an embodiment, the frame 110 may include multiple conductive areas. The conductive areas of the disclosure may be referred to as (one or more) electrodes.

According to an embodiment, the multiple electrodes may be disposed on at least a portion of the frame 110. For example, in case that the wearable device 100 is attached to a wrist of a user, two or more electrically separated electrodes (e.g., 201a and 201b) may be arranged on the lower surface in contact with the wrist of the user. For example, as shown in FIG. 2A, the multiple electrodes (e.g., 1 to 8) may be arranged at a predetermined (e.g., specified) interval on the upper surface or the lateral surface different from the lower surface. According to an embodiment, the shape and size of the electrode may be variably configured.

According to an embodiment, the display 120 may display biometric data of a user acquired through a biometric sensor. According to an embodiment, the display 120 may convert a screen output based on an input of the user with respect to a portion (e.g., a bezel) of the frame 110 or an input with respect to the display 120. For example, the display 120 may convert a watch screen into a biometric data screen (e.g., a body composition and a heart rate) in response to a user input.

According to an embodiment, the strap 130 may be connected to at least a portion of the frame 110 and detachably couple the wearable device 100 to a portion (e.g., a wrist, an ankle, and the like) of the user body. According to an embodiment, the user of the wearable device 100 may adjust the strap 130 to increase a degree of adhesion.

Figure 2B:
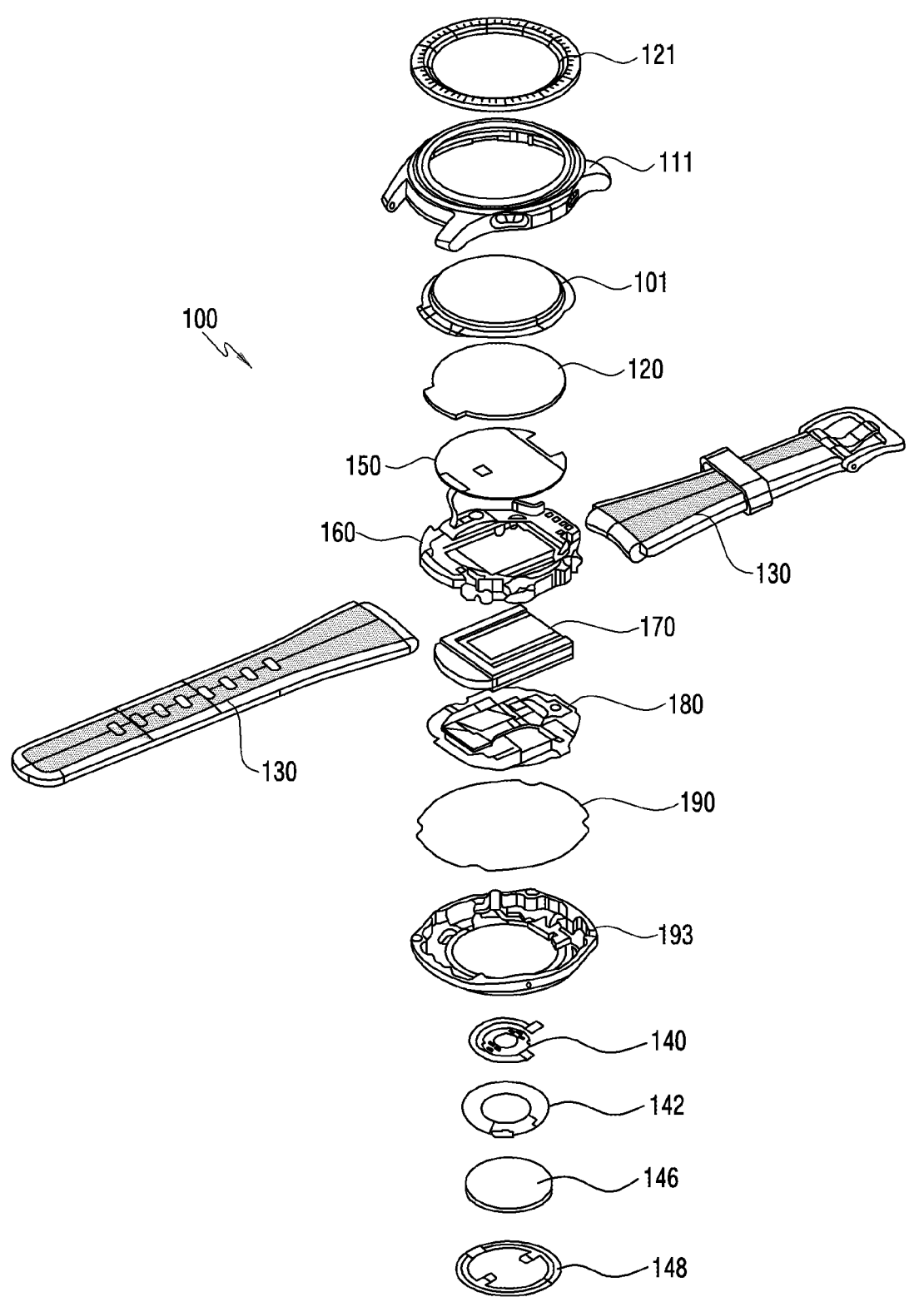
FIG. 2B is an exploded perspective view illustrating a wearable device according to various embodiments

FIG. 2B is an exploded perspective view illustrating a wearable device according to various embodiments.

Referring to FIG. 2B, the electronic device 100 may include a lateral bezel structure 111, a wheel key 121, a front plate 101, a display 120, an antenna 150, a support member 160 (e.g., a bracket), a battery 170, a printed circuit board 180, a sealing member 190, a rear plate 193, and a strap 130. The support member 160 may be disposed in the electronic device 100 to be connected to the lateral bezel structure 111 or integrally formed with the lateral bezel structure 111. The support member 160 may be formed of, for example, a metal material and/or a non-metal (e.g., polymer) material. The support member 160 may have the display 120 coupled to one surface thereof and the printed circuit board 180 coupled to the other surface thereof. A processor, a memory, and/or an interface may be mounted to the printed circuit board 180. The processor may include, for example, one or more of a central processing device, an application processor, a graphics processing unit (GPU), an application processor, a sensor processor, or a communication processor.

The memory may include, for example, a transitory memory or a non-transitory memory. The interface may include, for example, a high-definition multimedia interface (HDMI), a universal serial bus (USB) interface, an SD card interface, and/or an audio interface. The interface, for example, may electrically or physically connect the electronic device 100 to an external electronic device, and may include a USB connector, an SD card/MMC connector, or an audio connector.

The battery 170 is a device for supplying power to at least one component of the electronic device 100, and may include, for example, a non-rechargeable primary battery, or a rechargeable secondary battery, or a fuel cell. At least a part of the battery 170, for example, may be disposed on the substantially same plane as the printed circuit board 180. The battery 170 may be disposed and integrally formed in the electronic device 100 or may be disposed to be attachable to/detachable from the electronic device 100.

The antenna 150 may be disposed between the display 120 and the support member 160. The antenna 150 may include, for example, a near field communication (NFC) antenna, a wireless charging antenna, and/or a magnetic secure transmission (MST) antenna. The antenna 150, for example, may perform a near field communication with an external electronic device, wirelessly transmit and receive power required for charging, or transmit a magnetism-based signal including a near field communication signal or payment data. In an embodiment, an antenna structure may be formed of a part or a combination of the lateral bezel structure 111 and/or the support member 160.

The sealing member 190 may be disposed between the lateral bezel structure 111 and the rear plate 193. The sealing member 190 may be configured to block moisture and foreign substances from being introduced from the outside to a space surrounded by the lateral bezel structure 111 and the rear plate 193.

The biometric sensor 140 and the wireless charging coil 142 may be located between the rear plate 193 and the rear cover window 148. In an embodiment, the biometric sensor 140 and the wireless charging coil 142 may also be located between the sealing member 190 and the rear plate 193.

A grip sensor 146 may be located between the rear plate 193 and the rear cover window 148. According to an embodiment, the grip sensor 146 may be disposed on a portion other than the portion corresponding to the biometric sensor 140.

Figure 2C:
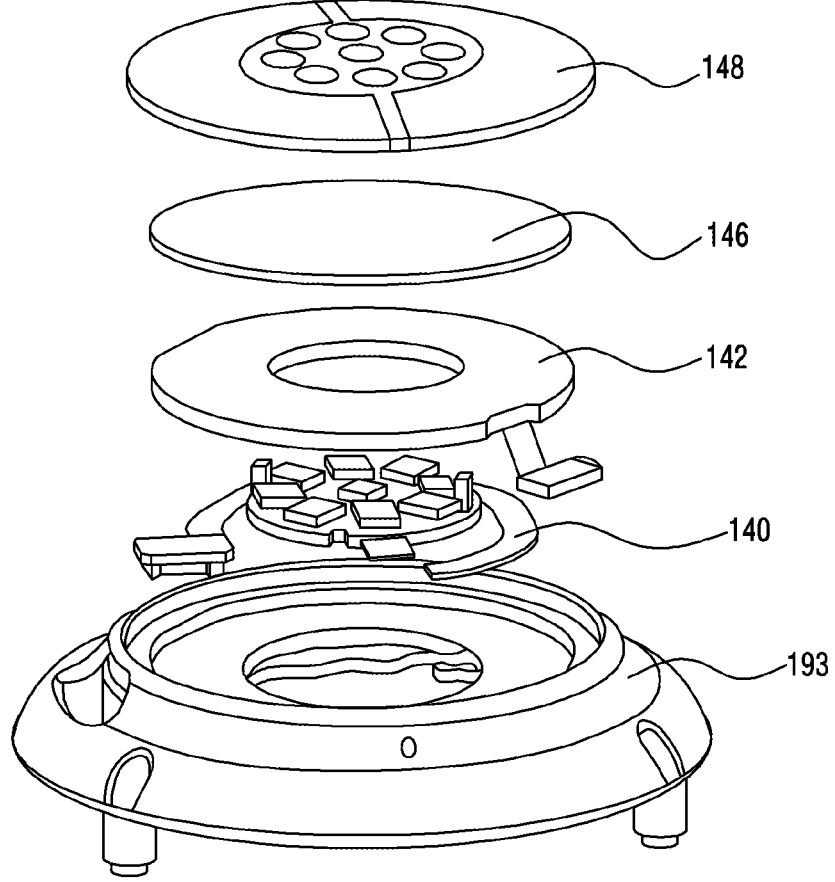
FIG. 2C is an exploded view illustrating a lower surface of a wearable device according to various embodiments.

FIG. 2C is an exploded perspective view illustrating a lower surface of a wearable electronic device according to various embodiments.

Referring to FIG. 2C, the rear plate 193, the rear cover window 148, the biometric sensor 140, the grip sensor 146, and the wireless charging coil 142 may be located on the lower surface of the wearable device (e.g., the wearable device 100 in FIG. 2A).

According to an embodiment, the rear plate 193 and the rear cover window 148 may be coupled to each other while forming an internal space. Various electronic components may be mounted in the internal space. For example, the biometric sensor 140, the grip sensor 146, and the wireless charging coil 142 may be located between the rear plate 193 and the rear cover window 148. According to an embodiment, in case that the biometric sensor 140 and the wireless charging coil 142 are arranged inside the electronic device 100 other than on the rear plate 193, the grip sensor 146 may have a configuration attached between the rear plate 193 and the rear cover window 148. According to an embodiment, two or more electrically separated electrodes (e.g., the electrodes 201a and 201b in FIG. 2A) may be arranged on the rear plate 193.

The structure of the above-described wearable device 100 is merely a non-limiting example and in various embodiments, the wearable device 100 may be implemented to have a structure different from those of FIG. 2A, FIG. 2B, and FIG. 2C. The wearable device 100 may have various shapes/ structures suitable for performing the method for measuring biometric data disclosed herein.

Figure 3A:
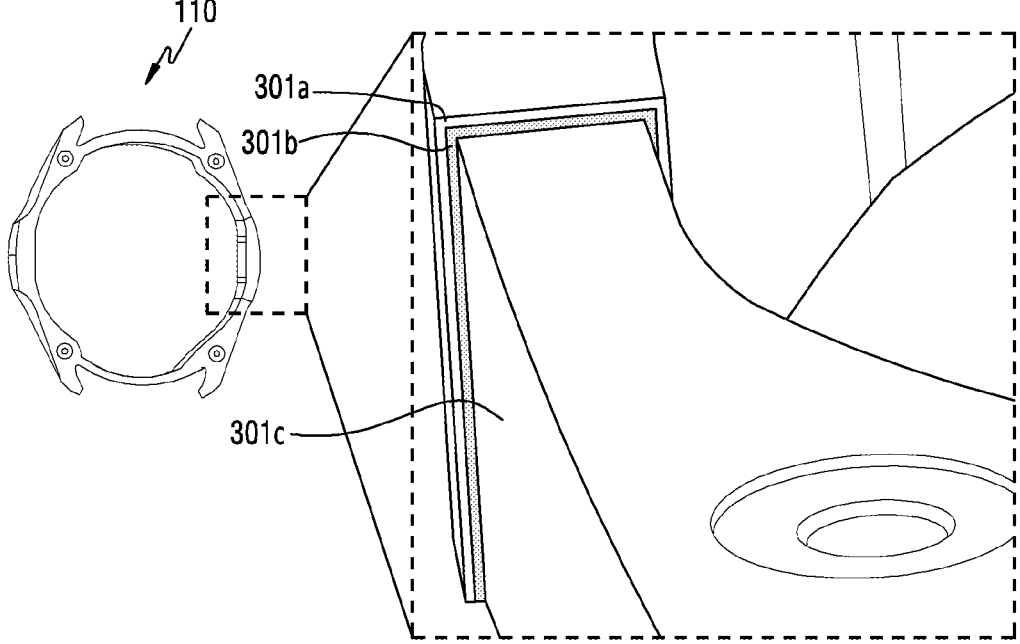
FIG. 3A and FIG. 3B are diagrams illustrating a frame structure of a wearable device according to various embodiments.
Figure 3B:
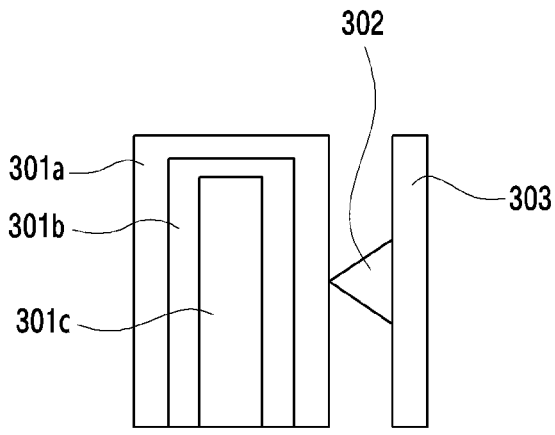

FIG. 3A and FIG. 3B are diagrams illustrating an example frame structure of a wearable device according to various embodiments.

Referring to FIG. 3A, the frame 110 according to an embodiment may be formed of a metal material 301c such as SUS or aluminum (Al). According to an embodiment, in case that the frame 110 is formed of a metal material, a non-conductive coating layer 301b may be disposed on a surface of the frame 110. For example, the non-conductive coating layer 301b may be separately manufactured and disposed to cover the metal material 301c of the frame 110 or may be formed by surface-treating the metal material 301c of the frame 110. According to an embodiment, the non-conductive coating layer 301b may correspond to a ceramic coating layer or a silicon dioxide (SiO$_2$) coating.

According to an embodiment, a conductive coating layer 301a may be disposed on at least a portion of the non-conductive coating layer 301b. For example, the conductive coating layer 301a may be separately manufactured to be disposed or may be formed by surface-treating the non-conductive coating layer 301b. According to an embodiment, the conductive coating layer 301a may be a coating including at least one of indium tin oxide (ITO), titanium (Ti), aluminum (Al), chromium (Cr), or chromium silicon nitride (CrSiCN).

Referring to FIG. 3B, in an embodiment, the conductive coating layer 301a may be formed in a shape surrounding a first surface facing the outside of the frame 110, a second surface facing an opposite side of a display (e.g., the display 120 in FIG. 1), and a third surface facing the inside of the frame 110. According to an embodiment, the conductive coating layer 301a may not be disposed on a surface facing the display 120 to prevent and/or reduce noise with other components.

According to an embodiment, the conductive coating layer 301a disposed on the third surface may be electrically connected to a printed circuit board 303 (e.g., the printed circuit board 180 in FIG. 2B) using a connector 302 provided on one side of the printed circuit board 303.

Figure 4A:
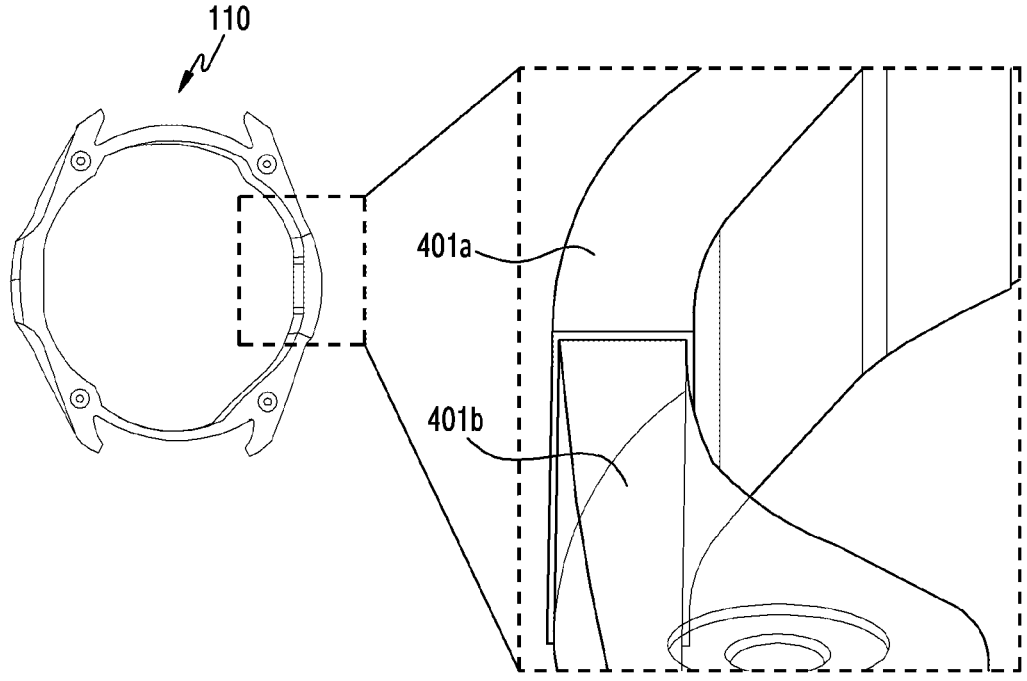
FIG. 4A and FIG. 4B are diagrams illustrating a frame structure of a wearable device according to various embodiments.
Figure 4B:
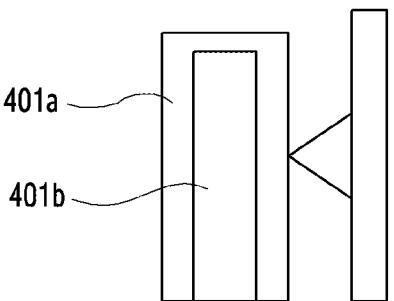

FIG. 4A and FIG. 4B are diagrams illustrating an example frame structure of a wearable device according to various embodiments.

Referring to FIG. 4A, the frame 110 according to an embodiment may be formed of a non-conductive material 401b such as gorilla glass, plastic, a synthetic resin. According to an embodiment, in case that the frame 110 is formed of a non-conductive material, a conductive coating layer 401a may be disposed on at least a portion of the frame 110. For example, the conductive coating layer 401b may be separately manufactured and disposed in a shape covering the non-conductive material 401b of the frame 110 or may be formed by surface-treating the non-conductive material 401b of the frame 110. According to an embodiment, the conductive coating layer 401a may be an indium tin oxide (ITO) coating or a chromium silicon nitride (CrSiCN) coating.

Referring to FIG. 4B, in an embodiment, the conductive coating layer 401a may be formed in a shape surrounding a first surface facing the outside of the frame 110, a second surface facing an opposite side of a display (e.g., the display 120 in FIG. 1), and a third surface facing the inside of the frame 110. According to an embodiment, the conductive coating layer 401a may not be disposed on a surface facing the display 120 to prevent and/or reduce noise with other components.

According to an embodiment, the conductive coating layer 401a disposed on the third surface may be in contact with a printed circuit board (e.g., the printed circuit board 180 in FIG. 2A or the printed circuit board 303 in FIG. 3B) using a connector (e.g., the connector 302 in FIG. 3B) provided on one side of the printed circuit board 303.

Figure 5:
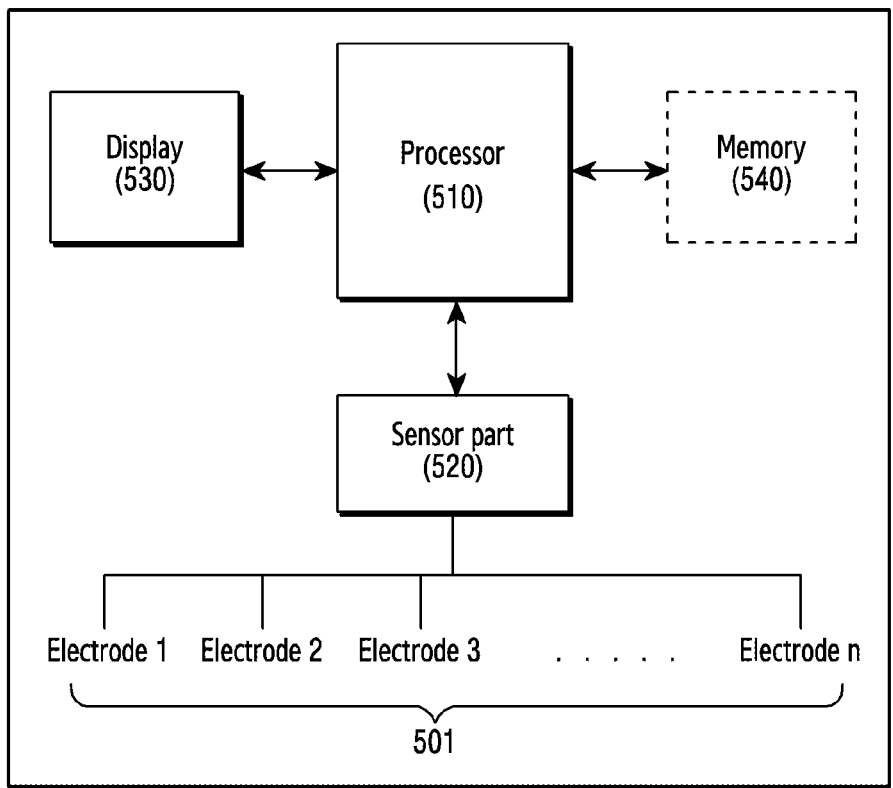
FIG. 5 is a block diagram illustrating an example configuration of a wearable device according to various embodiments.

FIG. 5 is a block diagram illustrating an example configuration of a wearable device according to various embodiments.

Referring to FIG. 5, the wearable device 100 may include a processor (e.g., including processing circuitry) 510, a sensor part (e.g., including at least one sensor) 520, a display 530, and a memory 540. In various embodiments, the wearable device 100 may include additional components other than the component described in FIG. 5 or omit at least one of the components described in FIG. 5.

According to an embodiment, the processor 510 may control at least one other component of the wearable device 100 and/or perform data processing or calculation with respect to communication, using instructions stored in the memory 540. According to an embodiment, the processor 510 may include at least one of a central processing unit (CPU), a graphic processing unit (GPU), a micro controller unit (MCU), a sensor hub, a supplementary processor, a communication processor, an application processor, an application specific integrated circuit (ASIC), and a field programmable gate array (FPGA), and may have multiple cores.

According to an embodiment, the processor 510 may include various processing circuitry and acquire biometric information (e.g., a heart rate, electrical skin response, an electrocardiogram, a bioelectrical resistance, electromyography (EMG)) of a user from a biometric sensor (e.g., the biometric sensor 140 in FIG. 2B) included in the sensor part 520. According to an embodiment, the processor 510 may receive a signal corresponding to a tap or a touch from a grip sensor (e.g., the grip sensor 146 included in FIG. 2B) included in the sensor part 520 and perform a designated operation based on the received signal. A detailed description related to the operation of the processor 510 may be given below with reference to FIG. 6.

According to an embodiment, the display 530 may display various contents (e.g., a text, an image, a video, an icon, and/or or a symbol, etc.). According to an embodiment, the display 530 may include, for example, and without limitation, a liquid crystal display (LCD), a light-emitting diode (LED) display, or an organic light-emitting diode (OLED) display. According to an embodiment, the display 530 may display biometric information of a user according to a command of the processor 510. According to an embodiment, the display 530 may provide a guide for a method for measuring biometric information according to a command of the processor 510. According to an embodiment, the display 530 may include a touch circuit (circuitry) configured to detect a touch or a sensor (e.g., a pressure sensor) configured to measure a strength of force generated by the touch. According to an embodiment, information collected through an interface of the display 530 may be processed by the sensor part 520.

According to an embodiment, the memory 540 may store various data acquired or used by at least one component (e.g., a processor) of the wearable device 100. For example, the memory 540 may store user biometric data acquired by the sensor part 520.

According to an embodiment, the sensor part 520 may include at least one sensor and detect a state of a user and output a signal corresponding to the detected state. According to an embodiment, the sensor part 520 may include a biometric sensor. For example, the biometric sensor may include one of an electrocardiography (ECG) sensor, a bioelectrical impedance (BIA) sensor, a galvanic skin response (GSR), an electromyography (EMG) sensor. According to an embodiment, the sensor part 520 may include a grip sensor.

According to an embodiment, the sensor part 520 may be electrically connected to multiple electrodes 501. According to an embodiment, at least one of the multiple electrodes 501 may be in contact with a first area of the user body. According to an embodiment, at least one of the multiple electrodes may be in contact with a second area of the user body other than the first area.

The sensor part 520 disclosed herein may be referred to as at least one sensor, a sensor circuit (circuitry), a sensor module, or the like.

Figure 6A:
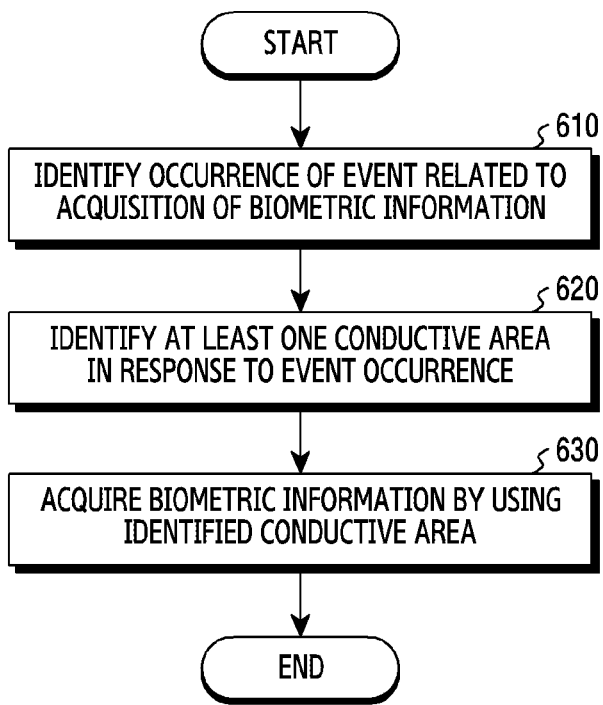
FIG. 6A is a flowchart illustrating an example of determining an electrode for measuring biometric information of a user in a wearable device according to various embodiments.

FIG. 6A is a flowchart illustrating an example of determining an electrode for measuring biometric information of a user in a wearable device according to various embodiments.

Referring to FIG. 6A, a processor (e.g., the processor 510 in FIG. 5) according to an embodiment may identify occurrence of an event related to acquisition of biometric information in operation 610. For example, the processor 510 may identify occurrence of an event in case that a first predetermined (e.g., specified) time has elapsed while at least one of the multiple electrodes is in contact with a portion of the user body.

According to an embodiment, in case that at least one of the multiple electrodes is in contact with a portion of the user body through a sensor part (e.g., the sensor part 520 in FIG. 5), the processor 510 may automatically identify occurrence of an event corresponding to the contact.

According to an embodiment, in case of detecting entering a measurement mode, the processor 510 may identify occurrence of an event corresponding to contact of a portion of the user body with at least one electrode among the multiple electrodes through the sensor part 520. According to an embodiment, a method for entering a measurement mode may correspond to one of execution of a biometric measurement menu, execution of an application, rotation of a wheel key (e.g., the wheel key 121 in FIG. 2B), and dragging with respect to the display 120.

According to an embodiment, in operation 620, in response to event occurrence, the processor 510 may identify at least one electrode (e.g., conductive area) related to the event occurrence. For example, the processor 510 may receive a signal corresponding to a user touch with respect to at least one of the multiple electrodes from the sensor part 520 and identify at least one of the multiple electrodes based on the received signal. According to an embodiment, in case that contact of the user is identified, the processor 510 may identify a selected electrode among the multiple electrodes, based on at least one of a contact location, a contact location change, a contact time point, and a contact completion time point.

According to an embodiment, in operation 630, the processor 510 may acquire biometric information of the user using the selected electrode (e.g., conductive area). According to an embodiment, each of the multiple electrodes may be connected to the biometric sensor through a multiplexer (MUX). According to an embodiment, in case that at least one electrode in contact with the user body is identified, the processor 510 may acquire biometric information of the user through the biometric sensor connected to the identified electrode. According to an embodiment, the configuration in which the multiple electrodes are connected to the biometric sensor may be varied through the multiplexer.

A detailed description related to connection between the multiple electrodes and the biometric sensor will be given below with reference to FIG. 7A.

Figure 6B:
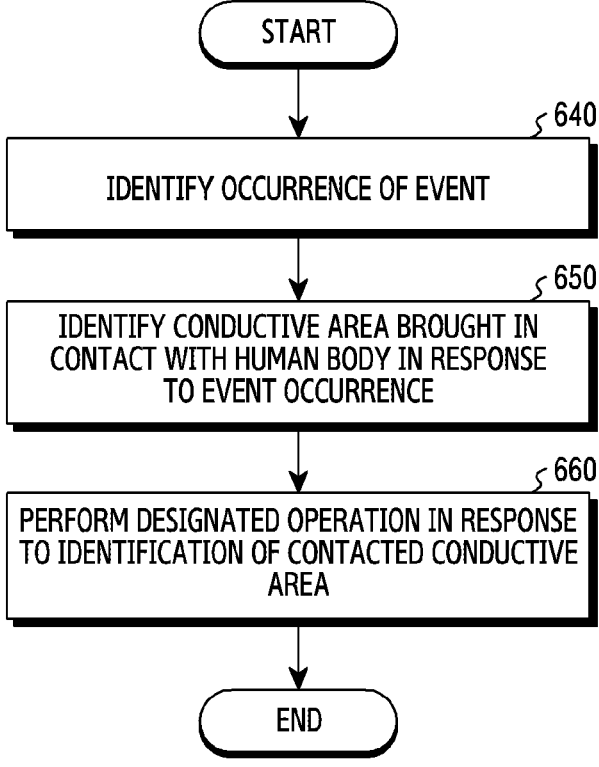
FIG. 6B is a flowchart illustrating an example of determining an electrode for performing a designated operation in a wearable device according to various embodiments.

FIG. 6B is a flowchart illustrating an example of determining an electrode for performing a designated operation in a wearable device according to various embodiments.

Referring to FIG. 6B, a processor (e.g., the processor 510 in FIG. 5) according to an embodiment may identify occurrence of an event in operation 640. According to an embodiment, the processor 510 may detect sequential touches with respect to the multiple electrodes or a tab or a touch with respect to at least one of the multiple electrodes. For example, a direction of sequential touches with respect to the multiple electrodes may include a clockwise direction or a counterclockwise direction.

According to an embodiment, in case that at least one of the multiple electrodes is in contact with a portion of the user body through a sensor part (e.g., the sensor part 520 in FIG. 5), the processor 510 may automatically identify occurrence of an event corresponding to the contact.

According to an embodiment, in case of detecting a measurement mode, the processor 510 may identify occurrence of an event corresponding to contact of a portion of the user body with at least one electrode among the multiple electrodes through the sensor part 520. According to an embodiment, a method for entering a measurement mode may correspond to one of execution of an application, rotation of a wheel key (e.g., the wheel key 121 in FIG. 2B), and dragging with respect to the display 120.

According to an embodiment, in operation 650, in response to event occurrence, the processor 510 may identify at least one electrode (e.g., conductive area) related to the event occurrence. For example, the processor 510 may receive a signal corresponding to a user touch with respect to at least one of the multiple electrodes from the sensor part 520 and identify at least one of the multiple electrodes based on the received signal. According to an embodiment, in case that a touch of the user is identified, the processor 510 may identify a selected electrode among the multiple electrodes, based on at least one of a touch location, a touch location change, a touch time point, and a touch completion time point.

According to an embodiment, in operation 660, the processor 510 may perform a designated operation in response to identification of the selected electrode (e.g., conductive area). According to an embodiment, each of the multiple electrodes may be connected to the grip sensor through a multiplexer (MUX). According to an embodiment, in case that at least one electrode related to occurrence of the event is identified, the processor 510 may perform a designated operation through the grip sensor connected to the identified electrode. For example, the designated operation may include turning on/off an electronic device, going back, changing a UI, changing the volume, or changing screen brightness.

A detailed description related to connection between the multiple electrodes and the grip sensor will be given below with reference to FIG. 7A.

Figure 7A:
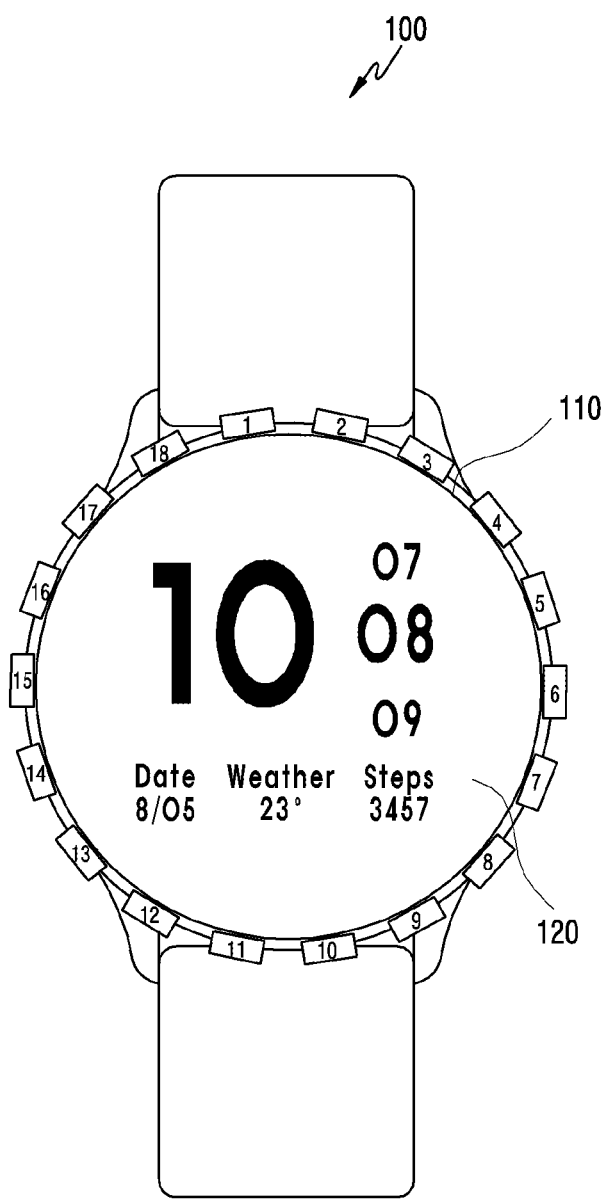
FIG. 7A, FIG. 7B and FIG. 7C are diagrams illustrating multiple electrodes included in a wearable device according to various embodiments.
Figure 7B:
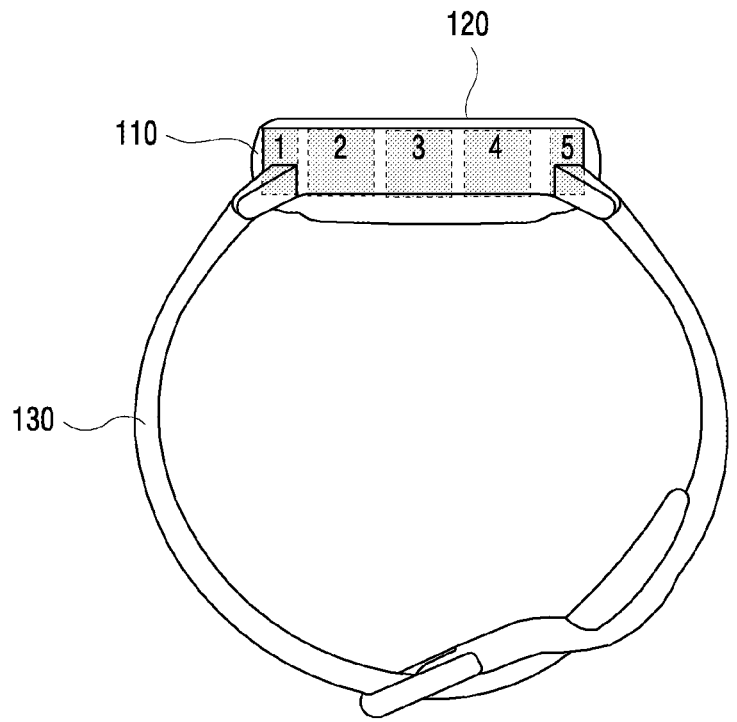
Figure 7C:
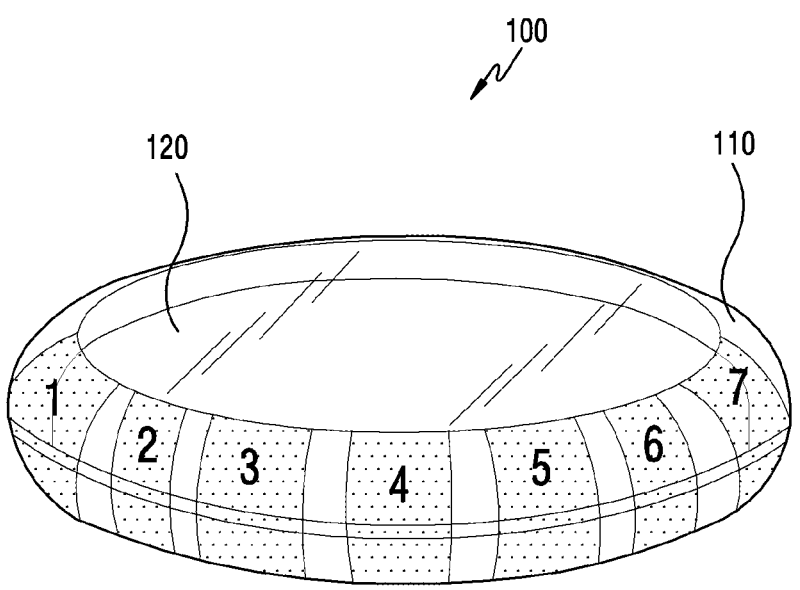

FIGS. 7A, 7B and 7C are diagrams illustrating multiple electrodes included in a wearable device according to various embodiments.

Referring to FIG. 7A, in an embodiment, multiple electrodes may be formed along an edge of the display 120. For example, as shown in FIG. 7A, electrode 1 to electrode 18 may be arranged at predetermined (e.g., specified) intervals along an edge of the display 120. According to an embodiment, at least one of the multiple electrodes may be disposed on a button of the wearable device 100. For reference, various electrodes described herein may be formed in the same manner as FIG. 3A, FIG. 3B, FIG. 4A, or FIG. 4B.

According to an embodiment, each of multiple biometric sensors may be electrically connected to at least one of the multiple electrodes. For example, and without limitation, electrode 1 to electrode 3 and electrode 10 to electrode 12 may be electrically connected to a BIA sensor, electrode 3 to electrode 5 may be electrically connected to an ECG sensor, and electrode 5 to electrode 7 and electrode 12 to electrode 14 may be electrically connected to a GSR sensor. According to an embodiment, an electrode (e.g., the electrode 201 in FIG. 2A) disposed on the lower surface may be electrically connected to the ECG sensor or the BIA sensor.

According to an embodiment, at least one grip sensor may be electrically connected to at least one of the multiple electrodes. For example, electrode 7 to electrode 9 may be electrically connected to a grip sensor functioning as a first key and electrode 10 to electrode 12 may be electrically connected to a grip sensor functioning as a second key.

In an embodiment, two or more electrodes among the multiple electrodes may be electrically connected to a grip sensor functioning as a wheel. For example, electrode 14 to electrode 18 may be electrically connected to a grip sensor functioning as a wheel.

Referring to FIG. 7B, in an embodiment, in case that the frame 110 is formed of a conductive material, the multiple electrodes may be arranged on the frame 110 surrounding at least a portion of the display 120. According to an embodiment, a non-conductive coating layer may be disposed on a surface of the frame 110 formed of a metal material and the multiple electrodes (e.g., 1 to 5) may be arranged at predetermined (e.g., specified) intervals on at least a portion of the non-conductive coating layer.

Referring to FIG. 7C, in an embodiment, in case that the frame 110 is formed of a non-conductive material, the multiple electrodes may be arranged on the frame 110 surrounding at least a portion of the display 120. According to an embodiment, the multiple electrodes (e.g., 1 to 7) may be arranged at predetermined intervals on at least a partial area of a surface of the frame 110 formed of a non-conductive material.

With respect to FIG. 7B and FIG. 7C, a description similar to or corresponding to the aforementioned description may be simplified or may not be repeated.

Figure 8:
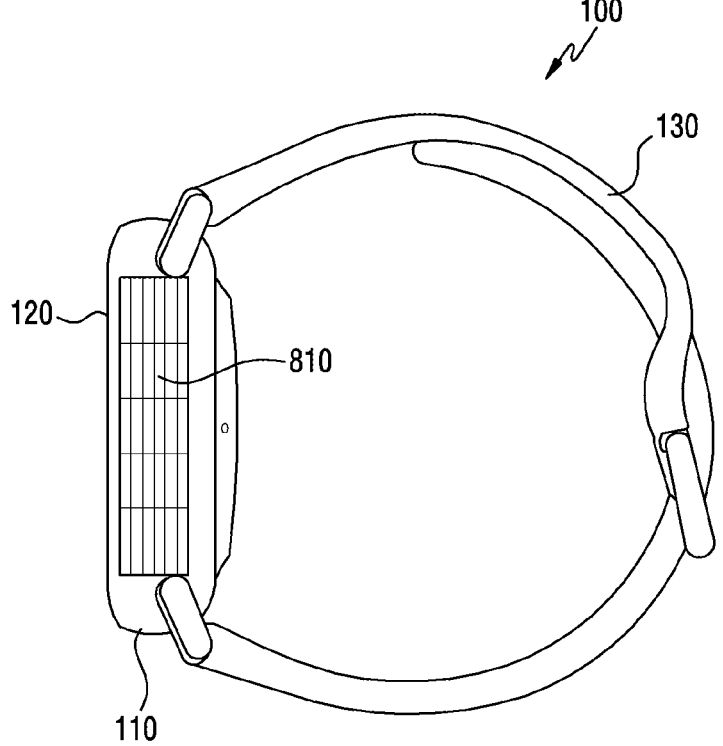
FIG. 8 is a diagram illustrating an arrangement state of multiple electrodes in a wearable device according to various embodiments.

FIG. 8 is a diagram illustrating an example arrangement state of multiple electrodes in a wearable device according to various embodiments.

Referring to FIG. 8, the multiple electrodes may be arranged on the frame 110 in a map shape 810. For example, the multiple electrodes may be arranged in a map shape 810 configured by m*n electrodes. According to an embodiment, the processor 510 may detect a user's touch with respect to an electrode of the map shape 810. According to an embodiment, the processor 510 may identify a touch scheme of the user and perform an operation designated based on the touch scheme. For example, the touch scheme of the user may include a touch flow in inverted-L, L, and Z directions and the processor 510 may perform a UX function corresponding to each touch scheme.

Figure 9A:
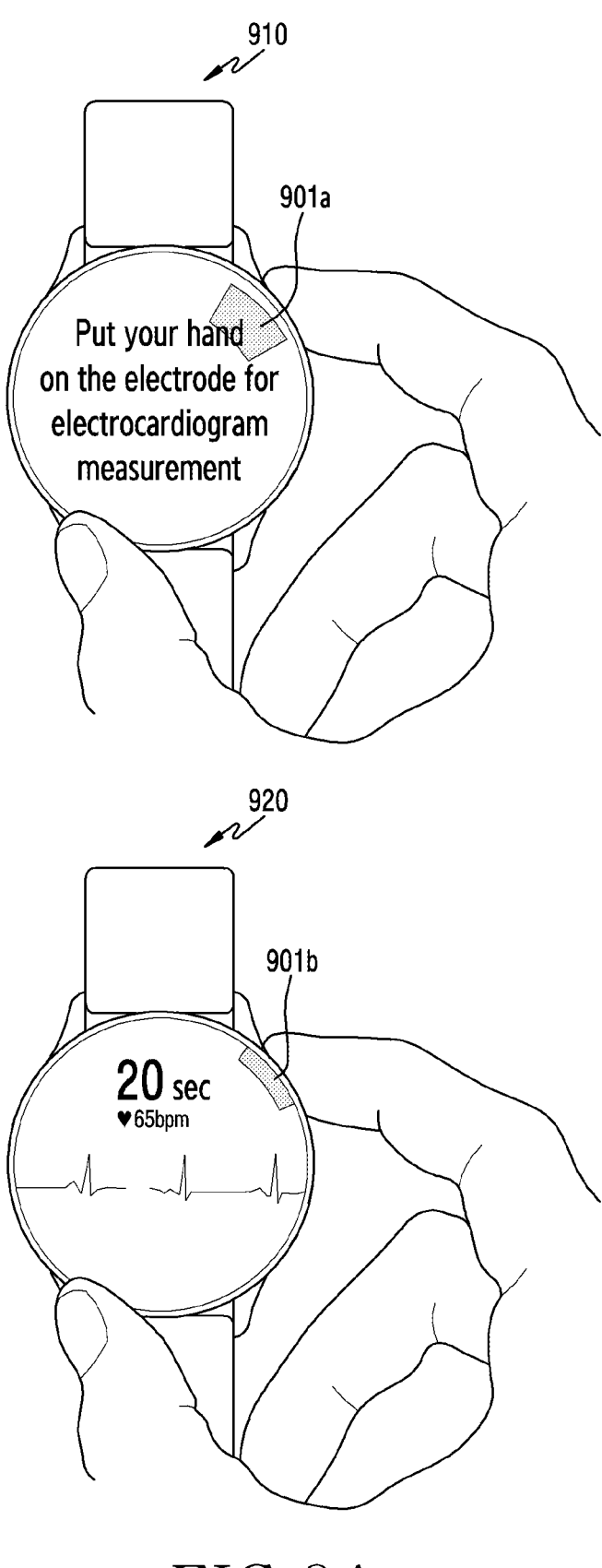
FIGS. 9A, 9B and 9C are diagrams illustrating example UIs provided on a display in a wearable device according to various embodiments.
Figure 9B:
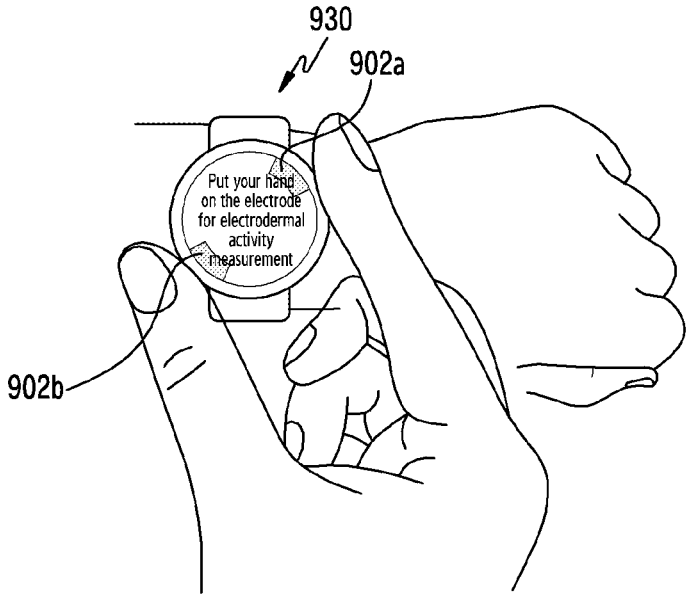
Figure 9B:
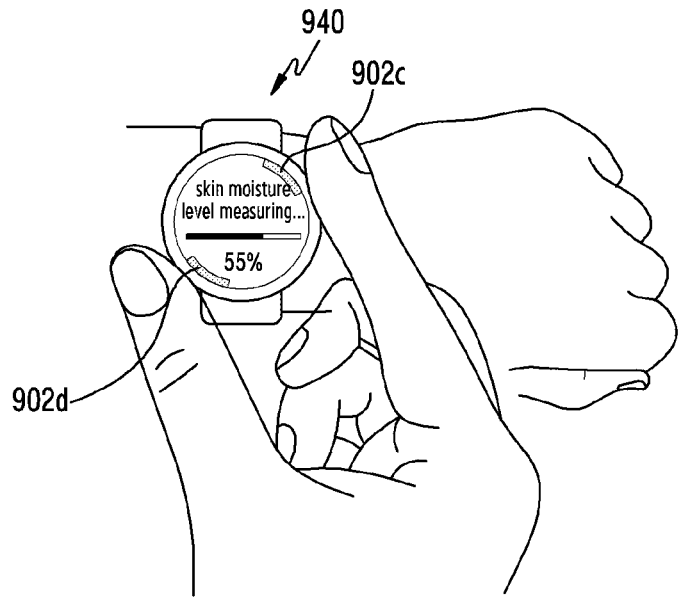
Figure 9C:
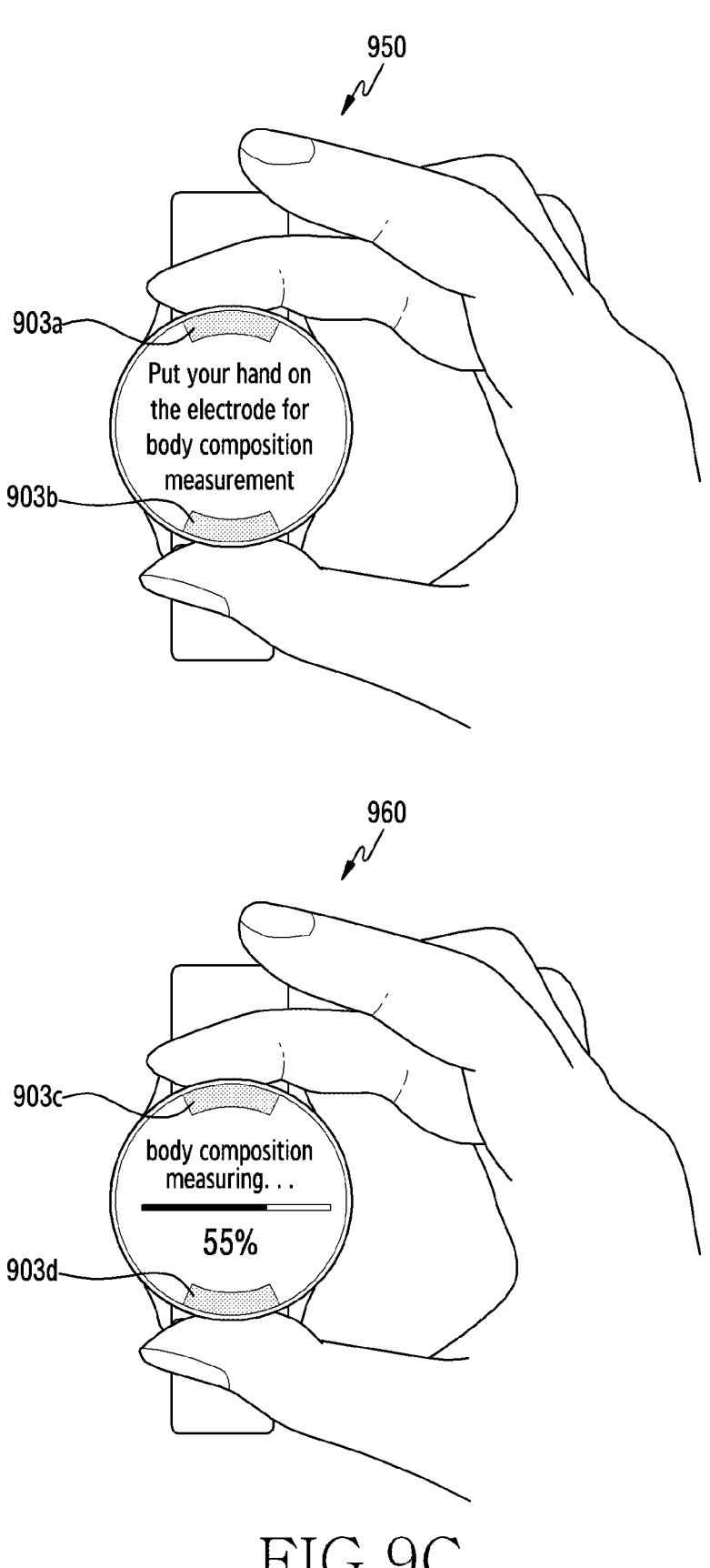

FIGS. 9A, 9B and 9C are diagrams illustrating example UIs provided on a display in a wearable device according to various embodiments. In relation to a description of FIGS. 9A, 9B and 9C, a description corresponding to, identical to, or similar to the aforementioned description may be simplified or may not be repeated.

Referring to FIG. 9A, a wearable device (e.g., the wearable device 100 in FIG. 1) according to an embodiment may measure user information through an ECG biometric sensor. According to an embodiment, as shown in a first screen 910 in FIG. 9A, the processor 510 may provide a guide for a contact position of the user. For example, the processor 510 may display a UI (e.g., 901a) with respect to a contact position of the user through the display 120.

According to an embodiment, as shown in a first screen 910 in FIG. 9A, the processor 510 may provide a guide for the user to bring the user body into contact with a correct position of an electrode. According to an embodiment, the processor 510 may output a guide message through the display 120. For example, the processor 510 may output a guide message (e.g., "Put your hand on the electrode for electrocardiogram measurement") for guiding the user to bring a finger in contact with a correct location.

According to an embodiment, as shown in a second screen 920 in FIG. 9A, in case of determining that the biometric information of the user is correctly measured, the processor 510 may continue measuring biometric information. For example, in case of detecting that the user body is brought in contact with two electrodes (e.g., the electrode 201 in FIG. 2A) arranged on the lower surface of the frame 110 or at least one of electrodes arranged on the upper surface or the lateral surface, the processor 510 may measure ECG information of the user using the ECG biometric sensor. According to an embodiment, the processor 510 may control and determine an electrode activated for biometric information measurement along a surface with which the user body is in contact.

According to an embodiment, the processor 510 may provide a UI with respect to a contact position of the user body. For example, the processor 510 may display a UI (e.g., 901b) with respect to a contact position of the user body through the display 120 while measuring biometric information of the user.

According to an embodiment, in case of determining that the biometric information of the user is normally measured, the processor 510 may output a guide message to the user through the display. For example, the processor 510 may output a guide message (e.g., "ECG measuring . . . ") to inform that the biometric information of the user is normally measured.

According to an embodiment, the processor 510 may provide an effect, such as a color, transparency, a shape, or haptic in the UI according to contact strength or a correct contact state to guide the user to make precise finger contact.

Referring to FIG. 9B, a wearable device (e.g., the wearable device 100 in FIG. 1) according to an embodiment may measure user information through an electrodermal activity (EDA) biometric sensor. According to an embodiment, as shown in a first screen 930 in FIG. 9B, the processor 510 may provide a guide for a contact position of the user. For example, the processor 510 may display a UI (e.g., 902a and 902b) with respect to a contact position of the user through the display 120.

According to an embodiment, as shown in a first screen 930 in FIG. 9B, the processor 510 may provide a guide for the user to bring the user body into contact with a correct position of an electrode. According to an embodiment, the processor 510 may output a guide message through the display 120. For example, the processor 510 may output a guide message (e.g., "Put your hand on the electrode for electrodermal activity measurement") for guiding the user to bring a finger in contact with a correct location.

According to an embodiment, as shown in a second screen 940 in FIG. 9B, in case of determining that the biometric information of the user is correctly measured, the processor 510 may continue measuring biometric information. For example, in case of detecting that the user body is brought in contact with at least two of electrodes arranged on the upper surface or the lateral surface of the frame 110, the processor 510 may measure a skin moisture level of the user using the GSR biometric sensor. According to an embodiment, the processor 510 may control and determine an electrode activated for biometric information measurement along a surface with which the user body is in contact.

According to an embodiment, the processor 510 may provide a UI with respect to a position with which the user body is in contact. For example, the processor 510 may display a UI (e.g., 902c and 902d) with respect to a contact position of the user's body through the display 120.

According to an embodiment, in case of determining that the biometric information of the user is normally measured, the processor 510 may output a guide message to the user through the display. For example, the processor 510 may output a guide message (e.g., "skin moisture level measuring . . . ") to inform that the biometric information of the user is normally measured.

According to an embodiment, the processor 510 may provide an effect, such as a color, transparency, a shape, or haptic in the UI according to contact strength or a correct contact state so as to guide the user to make precise finger contact.

Referring to FIG. 9C, a wearable device (e.g., the wearable device 100 in FIG. 1) according to an embodiment may measure user information through a BIA biometric sensor. According to an embodiment, as shown in a first screen 950 in FIG. 9C, the processor 510 may provide a guide for a contact position of the user. For example, the processor 510 may display a UI (e.g., 903a and 903b) with respect to a contact position of the user through the display 120.

According to an embodiment, as shown in a first screen 950 in FIG. 9C, the processor 510 may provide a guide for the user to bring the user body into contact with a correct position of an electrode. According to an embodiment, the processor 510 may output a guide message through the display 120. For example, the processor 510 may output a guide message (e.g., "Put your hand on the electrode for body composition measurement") for guiding the user to bring a finger in contact with a correct location.

According to an embodiment, as shown in a second screen 960 in FIG. 9C, in case of determining that the biometric information of the user is correctly measured, the processor 510 may continue measuring biometric information. For example, in case of detecting that the user body is brought in contact with two electrodes (e.g., the electrode 201 in FIG. 2A) arranged on the lower surface of the frame 110 or at least two of electrodes arranged on the upper surface or the lateral surface, the processor 510 may measure a body impedance of the user using the BIA sensor. According to an embodiment, the processor 510 may switch electrodes through the multiplexer (MUX) to control to perform a designated operation in any combination of electrodes.

According to an embodiment, the processor 510 may provide a UI with respect to a position with which the user body is in contact. For example, the processor 510 may display a UI (e.g., 903c and 903d) with respect to a contact position of the user's body through the display 120.

According to an embodiment, in case of determining that the biometric information of the user is normally measured, the processor 510 may output a guide message to the user through the display. For example, the processor 510 may output a guide message (e.g., "body composition measuring . . . ") to inform that the biometric information of the user is normally measured.

According to an embodiment, the processor 510 may provide an effect, such as a color, transparency, a shape, or haptic in the UI according to contact strength or a correct contact state to guide the user to make precise finger contact.

According to the embodiment described above, the wearable device 100 may support the user to intuitively recognize the contact position by providing the UI indicating a position of the electrode with which the user body is in contact.

Figure 10:
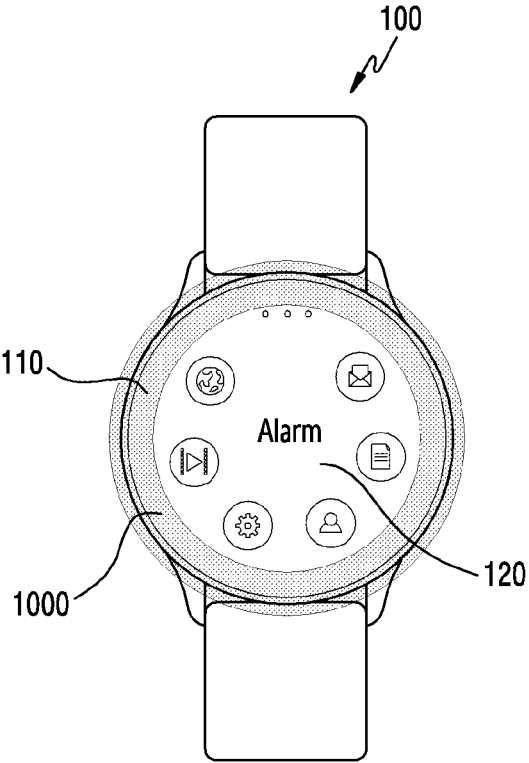
FIG. 10 is a diagram illustrating an arrangement state of multiple electrodes in a wearable device according to various embodiments.

FIG. 10 is a diagram illustrating an example arrangement state of multiple electrodes in a wearable device according to various embodiments.

Referring to FIG. 10, multiple electrodes according to an embodiment may be formed along an edge of the display 120 and the multiple electrodes may form a virtual bezel 1000. According to an embodiment, the processor 510 may provide a user interface (UI) corresponding to the multiple electrodes through the display 120. According to an embodiment, the processor 510 may determine an operation of the user, such as a touch, a swipe, or a squeeze with respect to the virtual bezel 1000 as a touch with respect to the multiple electrodes. According to an embodiment, the processor 510 may perform a function designated based on the touch scheme of the user.

According to the embodiment described above, the wearable device 100 may form the virtual bezel with the multiple electrodes and expand a touch area for the user.

Figure 11:
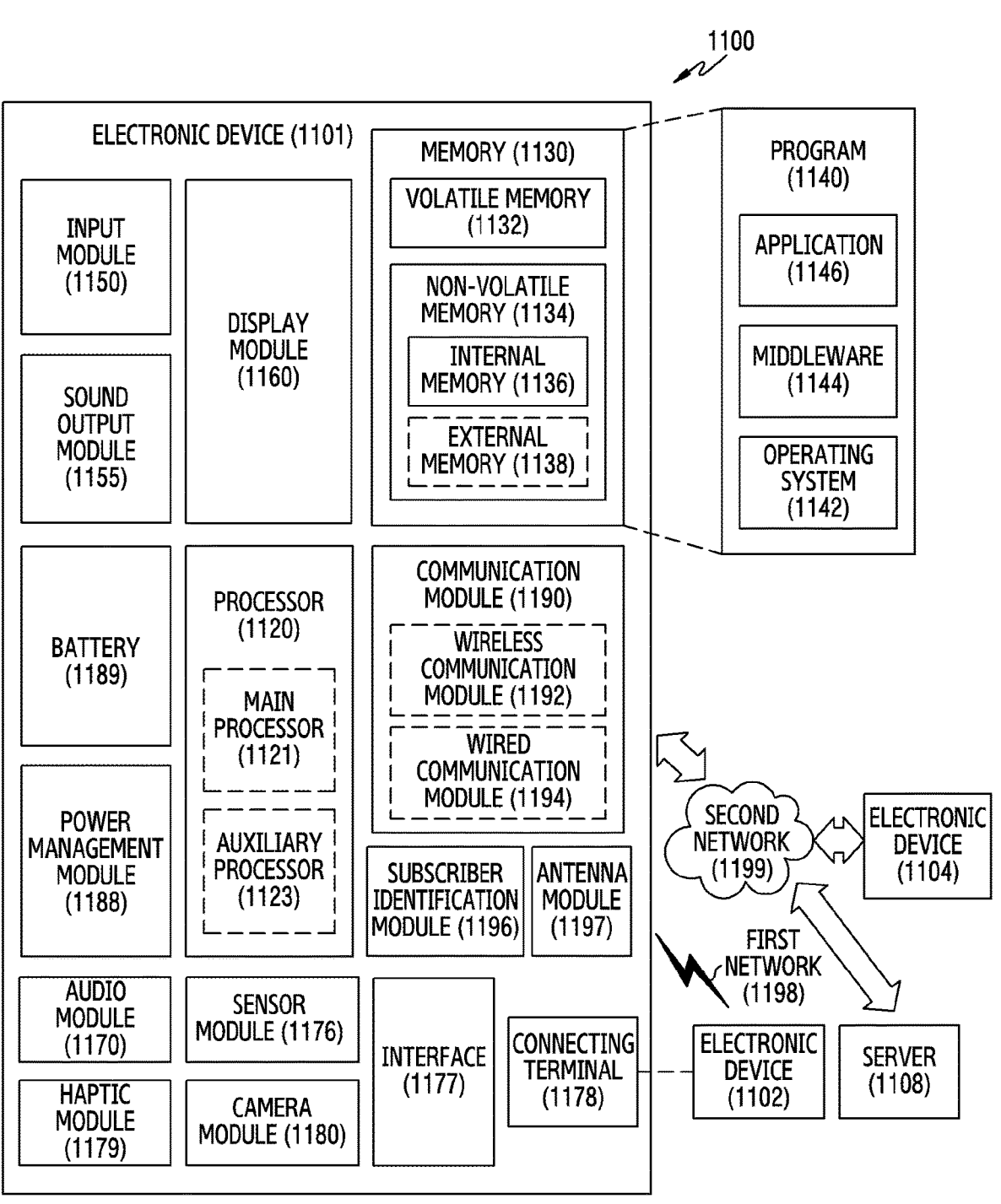
FIG. 11 is a block diagram illustrating an example electronic device in a network environment according to various embodiments.

FIG. 11 is a block diagram illustrating an example electronic device 1101 in a network environment 1100 according to various embodiments. Referring to FIG. 11, the electronic device 1101 in the network environment 1100 may communicate with an electronic device 1102 via a first network 1198 (e.g., a short-range wireless communication network), or at least one of an electronic device 1104 or a server 1108 via a second network 1199 (e.g., a long-range wireless communication network). According to an embodiment, the electronic device 1101 may communicate with the electronic device 1104 via the server 1108. According to an embodiment, the electronic device 1101 may include a processor 1120, memory 1130, an input module 1150, a sound output module 1155, a display module 1160, an audio module 1170, a sensor module 1176, an interface 1177, a connecting terminal 1178, a haptic module 1179, a camera module 1180, a power management module 1188, a battery 1189, a communication module 1190, a subscriber identification module (SIM) 1196, or an antenna module 1197. In various embodiments, at least one of the components (e.g., the connecting terminal 1178) may be omitted from the electronic device 1101, or one or more other components may be added in the electronic device 1101. In various embodiments, some of the components (e.g., the sensor module 1176, the camera module 1180, or the antenna module 1197) may be implemented as a single component (e.g., the display module 1160).

The processor 1120 may execute, for example, software (e.g., a program 1140) to control at least one other component (e.g., a hardware or software component) of the electronic device 1101 coupled with the processor 1120, and may perform various data processing or computation. According to an embodiment, as at least part of the data processing or computation, the processor 1120 may store a command or data received from another component (e.g., the sensor module 1176 or the communication module 1190) in volatile memory 1132, process the command or the data stored in the volatile memory 1132, and store resulting data in non-volatile memory 1134. According to an embodiment, the processor 1120 may include a main processor 1121 (e.g., a central processing unit (CPU) or an application processor (AP)), or an auxiliary processor 1123 (e.g., a graphics processing unit (GPU), a neural processing unit (NPU), an image signal processor (ISP), a sensor hub processor, or a communication processor (CP)) that is operable independently from, or in conjunction with, the main processor 1121. For example, when the electronic device 1101 includes the main processor 1121 and the auxiliary processor 1123, the auxiliary processor 1123 may be adapted to consume less power than the main processor 1121, or to be specific to a specified function. The auxiliary processor 1123 may be implemented as separate from, or as part of the main processor 1121.

The auxiliary processor 1123 may control at least some of functions or states related to at least one component (e.g., the display module 1160, the sensor module 1176, or the communication module 1190) among the components of the electronic device 1101, instead of the main processor 1121 while the main processor 1121 is in an inactive (e.g., sleep) state, or together with the main processor 1121 while the main processor 1121 is in an active state (e.g., executing an application). According to an embodiment, the auxiliary processor 1123 (e.g., an image signal processor or a communication processor) may be implemented as part of another component (e.g., the camera module 1180 or the communication module 1190) functionally related to the auxiliary processor 1123. According to an embodiment, the auxiliary processor 1123 (e.g., the neural processing unit) may include a hardware structure specified for artificial intelligence model processing. An artificial intelligence model may be generated by machine learning. Such learning may be performed, e.g., by the electronic device 1101 where the artificial intelligence is performed or via a separate server (e.g., the server 1108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 1130 may store various data used by at least one component (e.g., the processor 1120 or the sensor module 1176) of the electronic device 1101. The various data may include, for example, software (e.g., the program 1140) and input data or output data for a command related thereto. The memory 1130 may include the volatile memory 1132 or the non-volatile memory 1134.

The program 1140 may be stored in the memory 1130 as software, and may include, for example, an operating system (OS) 1142, middleware 1144, or an application 1146.

The input module 1150 may receive a command or data to be used by another component (e.g., the processor 1120) of the electronic device 1101, from the outside (e.g., a user) of the electronic device 1101. The input module 1150 may include, for example, a microphone, a mouse, a keyboard, a key (e.g., a button), or a digital pen (e.g., a stylus pen).

The sound output module 1155 may output sound signals to the outside of the electronic device 1101. The sound output module 1155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 1160 may visually provide information to the outside (e.g., a user) of the electronic device 1101. The display module 1160 may include, for example, a display, a hologram device, or a projector and control circuitry to control a corresponding one of the display, hologram device, and projector. According to an embodiment, the display module 1160 may include a touch sensor adapted to detect a touch, or a pressure sensor adapted to measure the intensity of force incurred by the touch.

The audio module 1170 may convert a sound into an electrical signal and vice versa. According to an embodiment, the audio module 1170 may obtain the sound via the input module 1150, or output the sound via the sound output module 1155 or a headphone of an external electronic device (e.g., an electronic device 1102) directly (e.g., wiredly) or wirelessly coupled with the electronic device 1101.

The sensor module 1176 may detect an operational state (e.g., power or temperature) of the electronic device 1101 or an environmental state (e.g., a state of a user) external to the electronic device 1101, and then generate an electrical signal or data value corresponding to the detected state. According to an embodiment, the sensor module 1176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 1177 may support one or more specified protocols to be used for the electronic device 1101 to be coupled with the external electronic device (e.g., the electronic device 1102) directly (e.g., wiredly) or wirelessly. According to an embodiment, the interface 1177 may include, for example, a high definition multimedia interface (HDMI), a universal serial bus (USB) interface, a secure digital (SD) card interface, or an audio interface.

A connecting terminal 1178 may include a connector via which the electronic device 1101 may be physically connected with the external electronic device (e.g., the electronic device 1102). According to an embodiment, the connecting terminal 1178 may include, for example, a HDMI connector, a USB connector, a SD card connector, or an audio connector (e.g., a headphone connector).

The haptic module 1179 may convert an electrical signal into a mechanical stimulus (e.g., a vibration or a movement) or electrical stimulus which may be recognized by a user via his tactile sensation or kinesthetic sensation. According to an embodiment, the haptic module 1179 may include, for example, a motor, a piezoelectric element, or an electric stimulator.

The camera module 1180 may capture a still image or moving images. According to an embodiment, the camera module 1180 may include one or more lenses, image sensors, image signal processors, or flashes.

The power management module 1188 may manage power supplied to the electronic device 1101. According to an embodiment, the power management module 1188 may be implemented as at least part of, for example, a power management integrated circuit (PMIC).

The battery 1189 may supply power to at least one component of the electronic device 1101. According to an embodiment, the battery 1189 may include, for example, a primary cell which is not rechargeable, a secondary cell which is rechargeable, or a fuel cell.

The communication module 1190 may support establishing a direct (e.g., wired) communication channel or a wireless communication channel between the electronic device 1101 and the external electronic device (e.g., the electronic device 1102, the electronic device 1104, or the server 1108) and performing communication via the established communication channel. The communication module 1190 may include one or more communication processors that are operable independently from the processor 1120 (e.g., the application processor (AP)) and supports a direct (e.g., wired) communication or a wireless communication. According to an embodiment, the communication module 1190 may include a wireless communication module 1192 (e.g., a cellular communication module, a short-range wireless communication module, or a global navigation satellite system (GNSS) communication module) or a wired communication module 1194 (e.g., a local area network (LAN) communication module or a power line communication (PLC) module). A corresponding one of these communication modules may communicate with the external electronic device via the first network 1198 (e.g., a short-range communication network, such as Bluetooth™ wireless-fidelity (Wi-Fi) direct, or infrared data association (IrDA)) or the second network 1199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 1192 may identify and authenticate the electronic device 1101 in a communication network, such as the first network 1198 or the second network 1199, using subscriber information (e.g., international mobile subscriber identity (IMSI)) stored in the subscriber identification module 1196.

The wireless communication module 1192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 1192 may support a high-frequency band (e.g., the mmWave band) to achieve, e.g., a high data transmission rate. The wireless communication module 1192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 1192 may support various requirements specified in the electronic device 1101, an external electronic device (e.g., the electronic device 1104), or a network system (e.g., the second network 1199). According to an embodiment, the wireless communication module 1192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 1197 may transmit or receive a signal or power to or from the outside (e.g., the external electronic device) of the electronic device 1101. According to an embodiment, the antenna module 1197 may include an antenna including a radiating element including a conductive material or a conductive pattern formed in or on a substrate (e.g., a printed circuit board (PCB)). According to an embodiment, the antenna module 1197 may include a plurality of antennas (e.g., array antennas). In such a case, at least one antenna appropriate for a communication scheme used in the communication network, such as the first network 1198 or the second network 1199, may be selected, for example, by the communication module 1190 (e.g., the wireless communication module 1192) from the plurality of antennas.

The signal or the power may then be transmitted or received between the communication module 1190 and the external electronic device via the selected at least one antenna. According to an embodiment, another component (e.g., a radio frequency integrated circuit (RFIC)) other than the radiating element may be 5 additionally formed as part of the antenna module 1197.

According to various embodiments, the antenna module 1197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 1101 and the external electronic device 1104 via the server 1108 coupled with the second network 1199. Each of the electronic devices 1102 or 1104 may be a device of a same type as, or a different type, from the electronic device 1101. According to an embodiment, all or some of operations to be executed at the electronic device 1101 may be executed at one or more of the external electronic devices 1102, 1104, or 1108. For example, if the electronic device 1101 should perform a function or a service automatically, or in response to a request from a user or another device, the electronic device 1101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 1101. The electronic device 1101 may provide the outcome, with or without further processing of the outcome, as at least part of a reply to the request. To that end, a cloud computing, distributed computing, mobile edge computing (MEC), or client-server computing technology may be used, for example. The electronic device 1101 may provide ultra low-latency services using, e.g., distributed computing or mobile edge computing. In an embodiment, the external electronic device 1104 may include an internet-of-things (IoT) device. The server 1108 may be an intelligent server using machine learning and/or a neural network. According to an embodiment, the external electronic device 1104 or the server 1108 may be included in the second network 1199. The electronic device 1101 may be applied to intelligent services (e.g., smart home, smart city, smart car, or healthcare) based on 5G communication technology or IoT-related technology.

The electronic device according to various embodiments may be one of various types of electronic devices. The electronic devices may include, for example, a portable communication device (e.g., a smartphone), a computer device, a portable multimedia device, a portable medical device, a camera, a wearable device, a home appliance, or the like. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via a third element.

As used in connection with various embodiments of the disclosure, the term "module" may include a unit implemented in hardware, software, or firmware, or any combination thereof, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 1140) including one or more instructions that are stored in a storage medium (e.g., internal memory 1136 or external memory 1138) that is readable by a machine (e.g., the electronic device 1101). For example, a processor (e.g., the processor 1120) of the machine (e.g., the electronic device 1101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

As described above, a wearable device (the wearable device 100 in FIG. 1) according to an example embodiment may include: a front surface of the wearable device including a display, a frame having the display seated therein and forming a lateral side of the wearable device, the frame including multiple conductive areas and a non-conductive area exposed between the multiple conductive areas, multiple biometric sensors arranged in a space formed by the frame and electrically connected to the multiple conductive areas, and a processor electrically connected to the multiple biometric sensors, wherein the processor is configured to: identify occurrence of an event related to acquisition of biometric information, identify, in response to the occurrence of the event, at least one conductive area for acquiring the biometric information among the multiple conductive areas, and acquire the biometric information using the identified at least one conductive area.

According to an example embodiment, the frame may include a non-conductive material and multiple areas of the frame may include a conductive material.

According to an example embodiment, the frame may include a conductive material, may include a non-conductive material, and the multiple areas of the frame may include a conductive material.

According to an example embodiment, at least one of the multiple conductive areas may be disposed on a surface configured to be in contact with a first portion of a body.

According to an example embodiment, the conductive material may at least partially surround a first surface facing outward of the frame, a second surface facing opposite to the display, and a third surface facing inward of the frame.

According to an example embodiment, the conductive material may not be included on a surface facing the display.

According to an example embodiment, the biometric sensor may include at least one of an electrocardiography (ECG) sensor, a bioelectrical impedance (BIA) sensor, and a galvanic skin response (GSR) sensor.

According to an example embodiment, the multiple conductive areas may be formed along an edge of the display and may be configured as a virtual bezel.

According to an example embodiment, contents to be displayed on the display may be controlled based on a touch input along the multiple conductive areas.

According to an example embodiment, a volume or brightness may be configured to be adjusted based on a touch continuously input along the multiple conductive areas.

According to an example embodiment, the wearable device may further include a memory and the processor may be configured to store the biometric information acquired from the biometric sensor in the memory.

According to an example embodiment, the processor may be configured to provide a notification related to the biometric information measurement.

According to an example embodiment, the notification may include a guide 5 for a measurement method provided through the display.

According to an example embodiment, based on the processor detecting that the first portion of the human body is in contact with at least one of the multiple conductive areas through the biometric sensor, biometric data measurement may be configured to be automatically started.

According to an example embodiment, based on detecting a measurement mode and detecting that the first portion of the body is in contact with at least one of the multiple conductive areas through the biometric sensor, the processor may be configured to start biometric data measurement.

As described above, a wearable device according to an example embodiment may include: a front surface of the wearable device including a display, a frame having the display seated therein and forming a lateral surface of the wearable device, the frame including multiple conductive areas and a non-conductive area exposed between the multiple conductive areas, at least one grip sensor arranged in a space formed by the frame and electrically connected to the multiple conductive areas, and a processor electrically connected to the at least one grip sensor, wherein the processor is configured to: identify occurrence of an event for executing a designated operation, identify, in response to the occurrence of the event, a conductive area in contact with a first portion of a body among the multiple conductive areas, and execute a designated operation in response to the identification of the contacted conductive area.

According to an example embodiment, the frame may include a non-conductive material and multiple areas may include a conductive material.

According to an example embodiment, the frame may include a conductive material, may include a non-conductive material, and the multiple areas of the frame may include a conductive material.

According to an example embodiment, the designated operation may include an operation of turning on/off the wearable device or an operation of going back.

According to an example embodiment, the conductive material may at least partially surround a first surface facing outward of the frame, a second surface facing opposite to the display, and a third surface facing inward of the frame.

While the disclosure has been illustrated and described with reference to various example embodiments, it will be understood that the various example embodiments are intended to be illustrative, not limiting. It will be further understood by those skilled in the art that various changes in form and detail may be made without departing from the true spirit and full scope of the disclosure, including the appended claims and their equivalents. It will also be understood that any of the embodiment(s) described herein may be used in conjunction with any other embodiment(s) described herein.

What is claimed is:
1. A wearable device comprising:
a display;
a frame configured to form a side of the wearable device and disposed to surround at least a portion of the display,
a conductive layer forming multiple conductive areas and disposed on the frame;
a non-conductive area visible between the multiple conductive areas;
multiple biometric sensors disposed in a space formed by the frame and electrically connected to the multiple conductive areas;
at least one processor comprising processing circuitry; and
memory storing instructions, when being executed by the at least one processor individually or collectively, cause the wearable device to:

identify occurrence of an event related to acquisition of biometric information;

identify, in response to the occurrence of the event, at least one conductive area for acquiring the biometric information among the multiple conductive areas; and acquire the biometric information using the identified at least one conductive area, wherein the conductive layer includes a first portion at least partially covering a first surface of the frame facing outward of the frame, a second portion at least partially covering a second surface of the frame facing opposite to the display, and a third portion at least partially covering a third surface of the frame facing inward of the frame, wherein the second portion of the conductive layer is extended from the first portion of the conductive layer, and wherein the third portion of the conductive layer is extended from the second portion of the conductive layer, wherein the first portion faces the third portion, and extends from a first end of the second portion, wherein the third portion extends from a second end of the second portion opposite to the first end of the second portion, and wherein at least a portion of the frame is positioned in a space formed by the first portion, the second portion and the third portion.

2. The wearable device of claim 1, wherein a non-conductive layer forms the non-conductive area, wherein the non-conductive layer includes a non-conductive material, and wherein the conductive layer includes a conductive material.

3. The wearable device of claim 1, wherein at least one of the multiple conductive areas is disposed on a surface configured to be in contact with a first portion of a body.

4. The wearable device of claim 2, wherein the conductive material is not included on a surface facing the display.

5. The wearable device of claim 1, wherein the biometric sensors comprise at least one of an electrocardiography (ECG) sensor, a bioelectrical impedance (BIA) sensor, and a galvanic skin response (GSR) sensor.

6. The wearable device of claim 1, wherein the multiple conductive areas are formed along an edge of the display, and the multiple conductive areas are configured as a virtual bezel.

7. The wearable device of claim 6, wherein a content to be displayed on the display is configured to be controlled based on a touch continuously input along the multiple conductive areas.

8. The wearable device of claim 6, wherein a volume or brightness is configured to be adjusted based on a touch continuously input along the multiple conductive areas.

9. The wearable device of claim 1, wherein the instructions, when being executed by the at least one processor individually or collectively, cause the wearable device to store the biometric information acquired from the biometric sensors in the memory.

10. The wearable device of claim 1, wherein the instructions, when being executed by the at least one processor individually or collectively, cause the wearable device to provide a notification related to the biometric information.

11. The wearable device of claim 10, wherein the notification comprises a guide for a measurement method provided through the display.

12. The wearable device of claim 1, wherein based on detecting that a first portion of a body is in contact with at least one of the multiple conductive areas through the biometric sensors, the instructions, when being executed by the at least one processor individually or collectively, cause the wearable device to automatically start biometric data measurement.

13. The wearable device of claim 1, wherein based on detecting a measurement mode and detecting that a first portion of a body is in contact with at least one of the multiple conductive areas through the biometric sensors, the instructions, when being executed by the at least one processor individually or collectively, cause the wearable device to start biometric data measurement.

* * * * *